United States Patent [19]
Salganik

[11] Patent Number: 5,484,589
[45] Date of Patent: Jan. 16, 1996

[54] ANTI-VIRAL METHODS USING RNASE AND DNASE

[75] Inventor: Rudolf I. Salganik, Novosbirsk, Russian Federation

[73] Assignee: Rufeld, Inc., Santa Monica, Calif.

[21] Appl. No.: 407,032

[22] Filed: Mar. 17, 1995

Related U.S. Application Data

[63] Continuation of Ser. No. 62,124, May 14, 1993, abandoned, which is a continuation-in-part of Ser. No. 870,686, Apr. 20, 1992, abandoned.

[51] Int. Cl.$^6$ .................................................. A61K 38/54
[52] U.S. Cl. ........................................ 424/94.2; 424/94.6
[58] Field of Search ................................ 424/94.2, 94.6; 435/236, 199

[56] References Cited

FOREIGN PATENT DOCUMENTS

| 4016483 | 11/1991 | Germany . |
| 9119789 | 12/1991 | WIPO . |

OTHER PUBLICATIONS

Trukhachov et al., Virology 3:552–555 (1967).
Glukhov et al., Arch. Neurol. 33:598–603 (1976).
Demin, Lancet, Jun. 26, 1976.
Colain et al., Ann. Oculist 203:371–378 (1970).
Gutorov et al., 1976.
Ehara et al., CA 106:116428, 1987.
Mink CA 82:106898, 1975.
Salganik, CA 73:32619, 1970.
Boerner et al., CA 111:28548, 1989.
Salganik et al., CA 85:103795, 1976.
D'Yachenko et al., BA 87(1):2190, 1988.

*Primary Examiner*—Marian C. Knode
*Assistant Examiner*—Jean C. Witz
*Attorney, Agent, or Firm*—Blakely, Sokoloff, Taylor & Zafman

[57] ABSTRACT

Methods for the treatment and prevention of human, animal and plant viral infections are provided. The methods consist of administering to an infected human, animal or plant an effective amount of DNase and RNase or other nuclease exhibiting properties of both enzymes, preferably in conjunction with a suitable divalent cation activator. The effective amount preferably provides a systemic or local concentration between about $5 \times 10^{-3}$ to $10 \times 10^{-3}$ Kunitz units of activity of each nuclease per ml of body fluids and between about 0.1 to 0.3 Kunitz units or more per ml of solution for incubating, growing, soaking or spraying plant seeds, microclones, seedlings or adult plants.

2 Claims, No Drawings

ANTI-VIRAL METHODS USING RNASE AND DNASE

This is a continuation of application Ser. No. 08/062,124, filed May 14,1993 now abandoned, which is a continuation-in-part of Ser. No. 07/870,686, filed Apr. 20, 1992, now abandoned.

BACKGROUND OF DE THE INVENTION

This invention relates to methods for prevention and treatment of animal vital infections and, more particularly, to methods of prevention and treatment of human, animal and plant viral infections by inhibiting viral DNA and RNA synthesis.

It is well established that all viruses can be divided into two main groups according to the nature of the nucleic acid, DNA or RNA, which they possess. Both types of viruses are infectious disease-causing agents that multiply only in cells. Multiplication of DNA viruses is often lethal to the host cell, causing cell lyses and concomitant release of new virus particles. Many clinical manifestations of viral infection reflect these cytolytic properties. RNA viral infection, on the other hand, generally leads to the nonlethal release of progeny viral products. DNA and RNA viruses also have profound effects on the genetic makeup of a host cell and can lead to the production of tumors and diseases such as viral encephalitis.

For many viral diseases, efficient drugs do not exist which specifically act on the vital life cycle. The majority of viral replication machinery is of host origin and, therefore, inhibition of the viral processes would also result in inhibition of host function. There are a limited number of drugs which have attempted to exploit subtle differences between viral and host mechanisms. Included among these drugs are nucleotide analogs such as 5-iododeoxyuridine, arabinosyl cytosine and acyclovir.

Most viruses enter the cell by endocytosis at coated pits and can be found inside the cell in endosomes surrounded by lipid membranes of cell origin. Inside the cell the viral nucleic acids become free of the protective viral protein coat and are potential targets for the hydrolytic action of a nuclease.

Nucleases are the enzymes which hydrolyze phosphodiester bonds in unprotected DNA or RNA molecules. Cleavage of viral nucleic acids results in the destruction of the viruses genetic information and loss of infectivity. Pancreatic DNase has been shown to inhibit synthesis of viral DNA and reproduction inside cells infected with DNA-containing viruses such as vaccinia, herpes and adenoviruses. Likewise, pancreatic RNase has been demonstrated to be an efficient means of inhibiting synthesis of viral RNA and reproduction of tick-born encephalitis, poliomyelitis, foot-and-mouth disease and other RNA-containing viruses.

When they appear in the extracellular space, the nucleases are captured by the cells and are endocytosed through the same mechanism as viral particles. When viruses and nucleases are present in the extracellular space at the same time, they can subsequently be found inside the same cytoplasmic endosomes where they can act on the viral nucleic acid. Since nucleases inside endosomes are isolated from cellular components, host DNA or RNA is not susceptible to their action. Additionally, DNA and RNA, as a rule, are packaged within complicated structures forming complexes with proteins which provides additional defense against nucleases if, for example, there is a leakage of nucleases from the endosomes. At the same time, the vital nucleic acids are much less protected inside the cell during replication and transcription outside of the endosomes. Thus, the use of these enzymes as antiviral agents is safe and essentially devoid of any cell damaging properties.

DNase and RNase have previously been tested for treatment of vital disease. Neither shows any cytopathogenic, antimitotic or mutagenic effects when added to nutritive medium of cell cultures or administered parenterally to animals in high doses. Embryotoxic, teratogenic or other toxic effects are also not observed with these enzymes in animals. Clinical trials have demonstrated high therapeutic efficiency of DNase in treatment of herpes zoster, herpes simplex, herpetic keratitis, infectious mononucleosis, adenoviral conjunctivitis and nasopharyngitis caused by DNA-containing viruses, while RNase was shown to be efficient in treatment of viral encephalitis and meningitis caused by RNA-containing viruses. RNase does not appear to be effective in treating DNA viruses.

Despite successful treatments of well characterized viral infections under controlled conditions, more often than not, clinical observations of vital diseases do not allow the identification of the specific causal agent. Virological methods, on the other hand, do allow the identification of the causal agent but are generally time consuming, complicated and, in many cases, not available. Additionally, there are clinical cases where two or more DNA and RNA viruses act together causing the infectious disease. An example is bronchopneumonia in calves where the DNA virus, adenovirus, acts synergistically with the RNA virus, parainfluenza virus. Other RNA viruses also play a role during the course of infection in bronchopneumonia.

There thus exists a need for a method of simultaneously treating or preventing viral infections caused by a wide variety of DNA or RNA viruses which is safe and effective for use in humans, animals and plants. The present invention satisfies this need and provides related advantages as well.

SUMMARY OF THE INVENTION

Methods for the treatment and prevention of human, animal and plant viral infections are provided. The methods consist of administering to an infected human, animal or plant an effective amount of DNase and RNase or other nuclease exhibiting properties of both enzymes, preferably in conjunction with a suitable divalent cation activator. The effective amount preferably provides a systemic or local concentration between about $5 \times 10^{-3}$ to $10 \times 10^{-3}$ Kunitz units of activity of each nuclease per ml of body fluids and between about 0.1 to 0.3 Kunitz units or more per ml of solution for incubating, growing, soaking or spraying plant seeds, microclones, seedlings or adult plants.

DETAILED DESCRIPTION OF THE INVENTION

The present invention is directed to methods for treating and preventing viral infections in humans, animals or plants caused by DNA and RNA viruses. The antiviral agent provided is a composition of DNase and RNase, preferably with a divalent cation activator. The method consists of treating an infected human, animal or plant with the antiviral DNase and RNase composition and is applicable for the treatment of either DNA or RNA viral infections or infections caused by the synergistic action of both types of viruses. The method is therefore advantageous for effective treatment when the virus cannot be clinically identified.

Additionally, administration of both DNase and RNase is superior to the treatment with either nuclease alone or the sum of their antiviral effects when they are applied separately since RNase enhances the antiviral effects of DNA.

In one embodiment, the antiviral agents are DNase and RNase isolated from an animal's pancreas having a specific activity from 3,000 to 5,000 Kunitz units per g or higher. The effective dosage of the antiviral agents is parenterally administered to a human or animal host in a delivery system which assures a systemic or local concentration between about $5 \times 10^{-3}$ to $10 \times 10^{-3}$ Kunitz units of a mixture of equal amounts of DNase and RNase per ml of body fluids.

In another embodiment, the present invention is directed to methods for treating superficial viral infections in animals by topically applying to the external surfaces of the infected animal a composition containing an effective antiviral amount of DNase and RNase composition with appropriate cations as enzymatic activators. By external surface of a human or animal is meant the skin, eye surfaces and mucosa membranes including, for example, the mouth, vagina, respiratory and gastro-intestinal tracts.

In a further embodiment, the present invention is directed to methods for treating plant seeds, microclones, seedlings or adult plants by incubating, growing, soaking or spraying such material with a solution containing DNase and RNase at concentrations between about 0.1 to 0.3 Kunitz units or more per ml of solution. The DNase and RNase activities can be contained within the same enzyme.

As used herein, the term "systemic" with regard to concentration, means the concentration of the antiviral agents per ml of body fluids.

As used herein, the term "local," with regard to concentration, means the concentration of antiviral agent per ml of body fluids at the cellular level of a discrete area within the body.

As used herein, the term "treatment" or "treating" means administration of an effective amount of a DNase and RNase composition to an animal already infected with a DNA or RNA animal virus.

As used herein, the term "preventing" means administering an effective amount of a DNase and RNase composition to an animal which is not yet infected or is infected with a latent DNA or RNA animal virus so as to inhibit infection.

As used herein "cation activator" refers to divalent cations which are required for nuclease activity as cofactors or augment the level of nuclease activity. Suitable divalent cation activators for use in the present invention include, for example, metal cations such as magnesium and manganese. Cation activators supplied as their corresponding salt are also included within this definition.

The invention provides a method for the treatment of animal virus infections which consists of administering to an infected subject an effective amount of DNase and RNase, preferably with a suitable divalent cation inhibitor. A method for preventing animal virus diseases is also provided. The animal can be a human.

In accordance with the practice of the method of the present invention, infections caused by viruses including, but not limited to, Paramixoviridae, Parvoviridae, Coronaviridae, Rhabdoviridae, Picornaviridae, Herpesviridae, Adenoviridae, Retroviridae and the like are susceptible to treatment or prevention by administering to the host an effective antiviral dose of DNase and RNase in conjunction with a suitable divalent cation activator.

The DNase and RNase components of the antiviral agent are administered together as a mixture so as to act synergistically in the inhibition of viral reproduction. The DNase and RNase activities can also be found within the same enzyme. Bacterial endonuclease isolated from Seratia marcescens is an example of such a nuclease. Alternatively, the DNase and RNase components can be consecutively administered over a relatively short period of time so as to still allow synergistic activity of the two nucleases. For example, instead of preparing and administering a single solution of DNase and RNase, a solution of DNase can be prepared and a separate solution of RNase can be prepared. Administration of one solution and then the other will provide the same antiviral effect as a mixture of both. Separate preparation of each nuclease component can be advantageous when different ratios of the nucleases are needed for different treatments.

The composition can be administered orally, such as with protective coatings, or it can be attached to carriers such as a water-soluble polymer, and injected into the subject. Administration by injection can include, for example, intravenous, subcutaneous, intramuscular and intracutaneous injection. Other types of administration can include, for example, topical, inhalation or by implantation into a body site or cavity. When the DNase and RNase composition, or other nuclease with properties of both enzymes, is used topically to treat, for example, superficial, cutaneous and mucosa membrane viral infection, it can be formulated into a pharmaceutically acceptable composition such as a lotion, cream, solution, emulsion, salve, suppositoria and the like. Additionally, it can be provided for administration in pharmaceutically acceptable mouthwash formulations for treating or preventing oral viral infections.

The optimal effective dosage of DNase and RNase administered for treatment or prevention of animal virus infections will depend on the size and body weight of the subject. Preferably, the dose delivered should be sufficient to obtain a systemic, local or topical concentration between about 3 to 7 Kunitz units per pound of body weight of each nuclease. The rate of delivery is preferably about 200 to 450 Kunitz units for a child of about 65 pounds for about 1 to 6 administrations, preferably about 3 to 6 administrations, more preferably about 3 to 4 administrations per day. The amount and rate of administration is dependent on the specific activity and stability of the enzyme preparations and is well within the determination of one skilled in the art given the effective dose range above. For example, smaller amounts of enzymes from preparations with higher specific activities can be used than that required for preparations having a lower specific activity. Treatment with the effective dose range should be continued until clinical symptoms are relieved. If additional infections occur, then treatment should be resumed. Alternatively, continued treatment following the disappearance of clinical symptoms can be advantageously used as a preventive measure of reoccurrence.

Although the method of this invention is described with respect to pancreatic DNase and RNase, practice of the principles of this invention is contemplated with antiviral agents which are equivalent to the above-mentioned nucleases in their properties to hydrolyze vital nucleic acids. The DNases and RNases are isolated preferably from beef or pig pancreas by methods well known in the art. Such methods include extraction of the enzymatic proteins from the minced pancreatic glands by a weak solution of sulfuric acid, stepwise precipitation of the enzymatic proteins by ammonium sulfate, purification of nucleases by chromatography and lyophilization of the enzymes. Alternatively, the nuclease components of the present invention can be produced by recombinant methods such as high level expression in a procaryotic expression system. Recombinant expression offers many advantages over classical biochemical purification of proteins and enzymes. For example, the nucleases can be efficiently produced in mass quantities due to the easy fermentation characteristics of bacteria and are more easily purified to homogeneity. DNase and RNase are also readily commercially available. commercial preparations of bacterial endonucleases with properties of DNase and RNase are also available.

A method for preventing viral diseases in plants is provided. The method includes administering to a plant an effective amount of DNase and RNase.

As with viral diseases in animals and humans, the antiviral agents described herein are equally applicable to the prevention or treatment of viral diseases in plants. One skilled in the art will know how to use such antiviral agents on plants and plant tissues. For example, DNase and RNase or other nucleases capable of splitting phosphodiester bonds of DNA and RNA can be topically applied to prevent or treat plant viral diseases. Plant seeds, microclones and seedlings can also be treated with the antiviral agents described herein. Methods of administering include, for example, incubating, growing, soaking, spraying or brushing a solution containing both DNase and RNase. An effective amount of each enzyme which can be administered is about 0.1 or more Kunitz units per ml of solution, preferably about 0.1 to 0.3 Kunitz units per ml of solution. Alternatively, the DNase and RNase activities can be substituted by a single enzyme which exhibits both properties of each individual enzyme. An example of such an enzyme exhibiting both activities is the bacterial endonuclease produced by Seratia marcescens.

The following examples are intended to illustrate but not limit the invention.

EXAMPLE I

This example shows the synergistic and complete inhibitory effect of nuclease treatment on vaccinia virus replication.

Cells prepared from newborn rabbit kidneys (RKC) were grown in flasks or on slides in test tubes. The growth medium contained 0.5% lactalbumin hydrolysate and inactivated bovine serum at a ratio of 9:1. Antibiotics were also contained in the media. Maintenance medium did not contain bovine serum. A 3-day RKC culture grown in flasks or on slides was washed with Hanks salt solution (HSS) and afterwards a vaccinia virus suspension was added at a multiplicity of infection of 1:10. The unabsorbed viral particles were removed after 2 hours of incubation at 37°C. by three washings with HSS and thereafter the maintenance medium was added.

To study the effect of nucleases on the synthesis viral DNA and reproduction of vaccinia virus, DNase (0.25 mg or 0.5 mg per ml), RNase (0.25 mg per ml) or a mixture of DNase (0.25 mg per ml) and RNase (0.25 mg per ml) were added to the maintenance medium. The pancreatic DNase which was used had a specific activity of 5,000–6,000 Kunitz units per g, while the specific activity of pancreatic RNase was 4,000–5,000 Kunitz units per g. Both enzymes were produced by the Leningrad Plant of Medical Preparations (Leningrad, USSR) isolated from beef pancreas by methods known in the art and briefly described above.

Thymidine incorporation was used as a measure of viral replication during the nuclease treatments. At 4, 8, 12 and 16 hours post infection, the maintenance medium was substituted by medium containing $^3$H-thymidine at a concentration of 5 µCi/ml (specific activity 3.7 Ci/mmole) and the flasks were incubated for one hour at 37° C. Thereafter the $^3$H-thymidine containing medium was discarded, the cell layer was washed three times with cold HSS and once with cold 5% perchloric acid. Cold and hot extractions with 5% perchloric acid were performed for 30 minutes at 4° C. and 90° C., respectively. The radioactivity of the extracts was measured with a scintillation counter.

Qualitative determinations of viral replication were also performed by autoradiography. For these experiments, slides with cell cultures were incubated for 30 minutes at 37° C. with $^3$H-thymidine (0.5 µCi/ml) at 4, 8, 12 and 16 hours post infection. The preparations were fixed in Carnoy's fixative, treated with 2% perchloric acid at room temperature for 40 minutes, and then photoemulsion was applied. The exposure took 2–4 weeks at 4° C. The preparations were stained with methylene blue after development. Two prepare ions were taken for each experimental point. In each of the preparations, the percentage of the labeled cells per 1,000 cells (the label index) was determined.

In vaccinia virus infected cells there is a peak of DNA synthesis at about 12 hours after infection. At this time period, the incorporation of $^3$H-thymidine into the DNA of infected cells exceeds by about by 3-fold the incorporation in uninfected cells. RNase treatment of infected cells resulted in a 14% decrease in the viral DNA synthesis during peak DNA synthesis. DNase treatment, on the other hand, inhibits DNA synthesis by 45% when used at a concentration of 0.25 mg/ml. Total inhibition of the virus induced DNA synthesis was obtained, however, when lower concentration of DNase was used in conjunction with RNase. Treatment with 0.25 mg/ml RNase resulted in total inhibition of viral DNA synthesis. These data indicate that there is a synergistic interaction between DNase and RNase. This was confirmed by the autoradiography experiments described below.

Vaccinia virus replicates only in the cytoplasm. Cytoplasmic replication of viral DNA allows the DNA synthesis due to viral replication alone to be determined because separate measurements of cellular (nuclear) and viral (cytoplasmic) DNA synthesis can be made. The autoradiography results revealed that viral DNA synthesis initiates at 4 hours after infection. At 16 hours post infection, the level of infected cells reaches about 40% (Table 1). Incorporation of $^3$H-thymidine into the nuclear DNA during this period is inhibited. This inhibition is primarily due to the overwhelming control of vaccinia virus replication over host synthesis machinery. Addition of DNase in amounts of 0.25 mg/ml to the maintenance medium considerably inhibited the synthesis of viral DNA in the cytoplasm and restored significantly the synthesis of nuclear DNA. Addition of RNase in amounts of 0.25 mg/ml inhibited the synthesis of viral DNA in cytoplasm to a lesser extent. Addition of DNase (0.25 mg per ml), in combination with RNase (0.25 mg per ml), essentially resulted in almost complete inhibition of vital DNA synthesis restoring at the same time the synthesis of nuclear DNA.

These results indicate that there is a synergistic interaction between DNase and RNase with respect to their inhibitory effect on the viral DNA synthesis.

TABLE 1

EFFECT OF DNase AND RNase ON THE SYNTHESIS OF VIRAL DNA
IN THE VACCINIA VIRUS (VV) INFECTED CELLS

| Hours after Infection | % of the $^3$H-thymidine labelled cells | | | | | | | |
|---|---|---|---|---|---|---|---|---|
| | 4 hours | | 8 hours | | 12 hours | | 16 hours | |
| | Nucleus | Cytoplasm | Nucleus | Cytoplasm | Nucleus | Cytoplasm | Nucleus | Cytoplasm |
| Control Cells | 26.4 ± 1.8 | — | 28.4 ± 1.2 | — | 27.9 ± 1.6 | — | 26.3 ± 1.2 | — |
| VV injected cells | 21.3 ± 1.1 | 5.2 ± 1.2 | 24.3 ± 1.9 | 9.2 ± 1.0 | 18.4 ± 2.0 | 16.2 ± 1.1 | 13.4 ± 1.1 | 36.2 ± 2.3 |
| VV injected cells, DNase 0.25 mg | 24.3 ± 1.5 | 2.3 ± 1.1 | 27.5 ± 1.1 | 5.6 ± 1.3 | 22.2 ± 0.8 | 9.4 ± 0.8 | 18.6 ± 1.0 | 12.1 ± 1.1 |
| VV injected cells, RNase 0.25 mg | 26.2 ± 1.4 | 4.1 ± 1.0 | 25.1 ± 0.9 | 7.1 ± 1.3 | 20.4 ± 1.1 | 12.0 ± 1.4 | 20.1 ± 0.9 | 22.3 ± 1.8 |
| VV infected cells, DNase 0.25 mg RNase 0.25 mg | 28.2 ± 1.7 | 1.1 ± 0.8 | 27.3 ± 1.0 | 1.5 ± 0.6 | 24.2 ± 0.9 | 3.2 ± 1.4 | 21.3 ± 1.8 | 5.2 ± 1.0 |

EXAMPLE II

This example shows the treatment of animals suspected of being infected with the DNA virus, parvovirus, or the RNA virus, paramixovirus, with a mixture of DNAse and RNAse. Dogs suspected to be infected by parvovirus, which causes gastroenteritis and/or myocarditis or by paramixovirus, which causes distemper were treated with a mixture of equal amounts of pancreatic DNase and RNase (DNase+RNase). The viral diagnoses were established on the basis of classical clinical symptoms (fever, diarrhea, anorexia, etc.). Under observation, 65 dogs became ill 3–5 days before the veterinary investigation. Among the 65 dogs, 36 animals were diagnosed as suffering of distemper resulting from paramixovirus infection. The remaining 29 animals were presumably infected by parvoviruses as diagnosed from clinical symptoms. The dogs were not vaccinated. Treatments with the pancreatic DNAse+RNAse mixed in equal amounts were administered in doses of 20 mg/injection diluted in 0.005% sterile solution of magnesium chloride. This dose was injected intramuscularly twice a day with a 7–9 hour interval for 3–4 days and combined with administration of antibiotics. All 20 non-treated animals of the control group died.

Administration of antibiotics alone was not efficient at all and, in most cases, did not save the animals from fatality. Only 1 of the 15 animals under investigation survived (94% mortality).

The administration of the DNase+RNase mixture resulted in a substantial improvement of the dogs state of health. The animals started to eat, to be more active, the intensity of diarrhea diminished. However, half of the 14 animals under investigation died (50% mortality).

Administration of the DNase+RNase mixture in conjunction with antibiotics was also tested. This treatment resulted in a rapid and substantial improvement of the dogs state of health. A few hours following the first injections, the animals started to eat and later to be active in their behavior, the diarrhea almost stopped in two days. Only 2 dogs of 36 died while all others recovered (5.0% mortality).

These results indicate that the mixed preparation of DNase and RNase may be applied in all cases where the viral disease is suspected but the virus is not identified precisely.

EXAMPLE III

Weakened children, prone to respiratory diseases, were taken from kindergarten groups to test preventive treatment using DNase+RNase mixtures. Respiratory diseases are more prevalent during the cold period of the year, and frequently break out in kindergarten affecting a number of children. Respiratory diseases are known to be caused by numerous viruses among which are DNA viruses such as adenoviruses and a number of RNA viruses such as influenza, parainfluenza, coxsackie viruses, echoviruses, rhinoviruses and some others. Two groups of 35 children each were formed to study the efficiency of the preventive treatment. The children in these groups were 4½ to 5 years old and the group was comprised of an equal number of girls and boys.

Usually each of the children became ill with respiratory disease twice or even three times during the late autumn and winter seasons during the last two or three years of observation. Children in one group were treated once per week by inhalation of aerosol of the DNase+RNase mixture where the enzymes were in equal amounts. The concentration of the composition was 2 mg/ml of each nuclease containing 0.005% $MgC_{12}$. About 1.5–2.0 ml of the solution was expended for one treatment. Children of the control group were treated in the same way by a placebo.

During three months of observation (from the beginning of November to the end of January) among the children of the control group there were two outbreaks of respiratory diseases and some of the children became ill twice, therefore, the total number of respiratory diseases amounted to 46.

Among the children treated by the DNase+RNase mixture there were only 4 cases of the respiratory diseases during this period in spite of contact between the children of both groups. Additionally, in spite of the manifold inhalations of the proteinaceous enzymatic composition, there were no allergic reactions. These results indicate a dramatic decrease compared to the control population in the occurrence of respiratory diseases due to preventative treatment with the DNAse+RNAse mixture.

A similar effect was achieved when children were treated twice per week by aerosol of bacterial endonuclease (10,000 E.A./ml in 0.005% $MgC_{22}$ solution) to prevent influenza. From 20 children treated in this way for a month during the outbreak of influenza, only one fell ill and the illness lasted only 5 days. From the control group of 15 children, 9 feel ill and the disease lasted on the average 10 days.

Almost the same results were achieved when adults were treated in a similar way. The adults used were medical doctors and their assistants who visited patients with influenza. From a sample of 62 adults, only 4 became infected and fell ill. In contrast, 9 adults from the control group of 18 subjects fell ill with influenza.

EXAMPLE IV

Bacterial endonuclease (BE) produced by Seratia marcescens (strain B10 M-1; Vector Company, Berdsk, USSR) possessing the activities of DNase and RNase was used for preventing plant viral diseases.

The kidney beans plants (Phaseolus vulgaris) were infected by the Southern bean mosaic virus (SBMV). The concentration of the virus in plant tissues was estimated by ELISA. BE was diluted in distilled water to get the final concentration 0.12–0.15 Kunitz units of RNase activity per ml. Tween was added to the solution to get the final concentration 0.01–0.1%. The solution of BE was applied topically on the leaves of the SBMV infected plants. The RNase activity was detected in different parts of the plant far from the application area and could be estimated in the plant tissues even at three weeks after a single application. At three weeks post BE treatment, the SBMV practically disappeared.

In a second experiment, potato tubers were infected by the potato mosaic virus (PMV). The concentration of the virus in tubers was estimated by ELISA test. The incisions were made on the tubers and the BE solution was applied topically. At three weeks, the potato tubers were free of the PMV.

EXAMPLE V

Bacterial endonuclease (BE) produced by Seratia marcescens with properties of RNase and DNase was used for improving the procedure of preparing viral-free plants via the apical meristem.

The BE was added to the Murashiga-Scooga medium used to grow the potato meristem. To prepare 100 ml of the BE containing medium, 100.000 Kunitz units of sterile lyophilized BE were dissolved in 10 ml of sterile distilled water. Dry components of the standard nutritive medium for preparing 100 ml of the latter were dissolved in 90 ml of distilled water and sterilized by autoclaving. When the medium was cooled to about 45° C., the solution of BE (10ml) was added. To 100 ml of the prepared nutritive medium 0.5 ml of 20% sterile solution of $MgSO_4$ was added where $Mg^{2+}$ serves as an activator of BE. The potato meristems just after isolation from tuber seedings were placed on the nutritive medium for 4–6 weeks till they started to grow. Thereafter the meristems were transferred to the standard nutritive medium which did not contain BE. In 30–40 days when regenerating sprouts appeared, they were transferred to the third medium for rooting the sprouts. When the sprouts reached 10–12 cm, the apical parts, internodes, were cut off and planted into the tubes with a medium for grafts. The rest of the plant was used to estimate the concentration of viruses.

TABLE 2

EFFECT OF BE ON THE YIELD OF POTATO PLANTS REGENERATED FROM THE APICAL MERISTEMS AND AMOUNT OF VIRUS-FREE PLANTS

| Potato variety | Experimental conditions | No. of meristems cultivated | No. of plants regenerated (%) | No. of virus-free plants (%) |
|---|---|---|---|---|
| Polyot | Control | 35 | 5 (14) | 1 (20) |
|  | BE | 56 | 17 (30) | 7 (41) |
| Kemerovsky ranny | Control | 37 | 4 (11) | 1 (25) |
|  | BE | 47 | 13 (28) | 6 (46) |

The BE not only increases the number of viral-free plants, but it also stimulated substantially the regeneration of plants from meristems and their morphogenesis.

Growing of grafts for 20 days in the medium with BE (200 Kunitz units/ml) also resulted in a decrease of the concentration of viruses in microcloned plants. For this purpose, the apical parts, internodes, of the grafts grown for 20 days were twice transferred to the fresh medium with BE. The concentration of viruses estimated by ELISA in most plants went down to the figures which are characteristic for the practically healthy plants.

Growing of the graft in the BE containing nutritive medium stimulates later the plant growth and yield of tubers.

TABLE 3

EFFECT OF THE BE ON THE YIELD OF POTATO TUBERS

| Potato variety | Experimental conditions | Yield Weight, g | No. of tubers per plant |
|---|---|---|---|
| Polyot | Control | 72.3 ± 1.9 | 9.8 ± 0.4 |
|  | BE | 200.0 ± 3.6 | 13.9 ± 0.7 |

Example VI

This example further demonstrates the synergistic properties of RNase and DNase, in this case on the RNA virus VSV (vesicular stomatitis virus). Embryonic Fibroblast cultures were infected with 100 plaque forming units (PFU) per mL of VSV. As seen in the table, the VSV titre is measured on a $Log_{10}$ scale. 0.1 mg/mL RNase and 0.1 mg/mL DNase were added to the culture alone and in combination, and incubated for 24 hours. The results show significant reduction of VSV with RNase administration, and no reduction (compared to control) with DNase administration. These data are not unexpected given the known effectiveness of nucleases against RNAviruses. Unexpectedly, the combination of RNase and DNase dramatically improves on the ability of RNase alone to reduce VSV, by two orders of magnitude.

TABLE VI-1

| VSV infected cells | VSV titre as log (PFU/mL) |
|---|---|
| Control | 8.8 |
| +RNase | 5.2 |
| +DNase | 8.5 |
| +RNase and DNase | 3.3 |

Although the invention has been described with reference to the presently preferred embodiment, it should be understood that various modifications can be made without departing from the spirit of the invention. Accordingly, the invention is limited only by the following claims.

I claim:

1. A method for treating a dog infected by a canine viral infection selected from the group consisting of parvovirus and parvomixovirus comprising administering to said infected dog a therapeutically effective amount of DNase and RNase.

2. The method of claim 1 wherein said DNase and RNase is formulated by dissolving 10 mg of DNase and 10 mg of RNase in a sterile solution of $0.005 MgCl_2$; adding antibiotics to the RNase and DNase solution; and is administered by intramuscular injection.

* * * * *